United States Patent [19]

Bhat

[11] Patent Number: 5,800,993
[45] Date of Patent: Sep. 1, 1998

[54] DNA SEQUENCING APPARATUS AND METHOD FOR A SMALL FORMAT GEL WITH A MAGNIFIED READOUT

[75] Inventor: Suraj P. Bhat, Los Angeles, Calif.

[73] Assignee: The Regents of the University of California, Oakland, Calif.

[21] Appl. No.: 685,777

[22] Filed: Jul. 23, 1996

Related U.S. Application Data

[63] Continuation of Ser. No. 282,610, Jul. 29, 1994, abandoned.

[51] Int. Cl.[6] ................................................. C12Q 1/68
[52] U.S. Cl. ........................... 435/6; 204/461; 204/466
[58] Field of Search .................................. 204/466, 467, 204/461; 435/6

[56] References Cited

U.S. PATENT DOCUMENTS

| | | | |
|---|---|---|---|
| 4,592,089 | 5/1986 | Hartman | 382/6 |
| 4,841,443 | 6/1989 | Kakumoto et al. | 364/413.01 |
| 4,884,200 | 11/1989 | Kimura et al. | 364/413.13 |
| 4,908,307 | 3/1990 | Rodland et al. | 435/6 |
| 5,234,559 | 8/1993 | Collier et al. | 204/182.8 |
| 5,260,190 | 11/1993 | Shiraishi et al. | 435/6 |
| 5,281,517 | 1/1994 | Bacus et al. | 435/6 |
| 5,424,186 | 6/1995 | Fodor et al. | 435/6 |

OTHER PUBLICATIONS

Sambrook et al., Molecular Cloning, Cold Spring Harbor Laboratories, p. 13.45, 1989.

*Primary Examiner*—Scott W. Houtteman
*Attorney, Agent, or Firm*—Daniel L. Dawes

[57] ABSTRACT

The time, difficulty, and expense of running DNA sequencing gels is substantially reduced by running the DNA sequence in a minigel of approximately 8×11 cm at a reduced electrophoretic voltage and without preheating the buffer solution in contact with the gel. The image produced from the sequence gel or autoradiograph is then scanned with a CCD line camera. The pixel map of the autoradiograph image is then magnified using software techniques within the computer so that it is displayed on the CRT screen at an increased scale permitting easy visual separation between the DNA bands.

21 Claims, 4 Drawing Sheets

WINDOW 10, MATCHES 5, KtUP 5, SPEED 1

WINDOW 10, MATCHES 5, KtUP 5, SPEED 1

DNA SEQUENCING APPARATUS AND METHOD FOR A SMALL FORMAT GEL WITH A MAGNIFIED READOUT

This is a continuation of application Ser. No. 08/282,610 filed on Jul. 29, 1994 now abandoned.

This invention was made with Government support under NIH Grant EY06044 awarded by the National Institutes of Health. The Government has certain rights in this invention.

BACKGROUND OF THE INVENTION

1. Field of the Invention

The invention relates to DNA sequencing apparatus and methodologies, and in particular to a small format gel with a magnified readout.

2. Description of the Prior Art

DNA sequencing strategies and methodologies have undergone significant evolution since the technique was first developed more than 15 years ago. Improvements have mostly come in the areas of new chemicals, enzymes, readout systems, and computer assisted reading and compiling of data. Despite these many changes, discrimination between incrementally sized, labelled oligonucleotide fragments still primarily uses a large size format, slab gel electrophoresis system, typically with a gel of the order of about 25 cm by 40 cm. It was believed that the use of such large gels was necessary in order to be able to reliably separate the DNA fragments and read them.

The large format gel which is commonly employed in DNA sequencing involves very high voltages, large volumes of buffer and appreciable expenditure of time, materials and bench space in order to successfully manipulate. Both manual and automated sequencing protocols demand stringent expertise with at least two to three hours for the preparation of the gel cassette and other cumbersome chores before the actual electrophoresis can be started. See for example the teachings set forth by Applied Biosystems, Inc., DNA Sequence System, Users Manual at 373 (1990–92); and J. Sambrook et al., Molecular Cloning: A Laboratory Manual, Cold Spring Harbor Laboratory, Cold Spring Harbor, N.Y. (1989). In manual sequencing, postelectrophoresis handling of the gels is clumsy and fraught with potential mishaps, due directly or indirectly in a large part because of the large size format.

The short protocol for running the conventional large format gel is a sequence of at least 46 steps in which prewarming the gel and even elevating its temperature to the highest possible level is taught as a means for eliminating compressions. The conventional dideoxy sequencing protocol is designed so that it can be carried out in a single long day as part of a daily routine in the midst of a large scale sequencing project. In general, if a large region of DNA is to be sequenced, the sequencing is usually carried out as part of a concerted effort. DNA sequencing in conventional methodologies is easier, more efficient and more successful when a daily rhythm has been acquired.

A day's work start with developing the autoradiographs of the sequencing gels from the previous day. Then, template-primer reactions are set up. Next, gels are poured and the primer extension reaction started. When these are complete, reactions are loaded onto the gels, by which time it is generally noon. After lunch hour, the gels are stopped, dried down and put on a film over night. The day ends by cleaning the gel plates and setting them up for the next day. In all, the process takes 7 to 8 hours for 10 templates, and 9 to 10 hours for 20 templates. See F. Ausubel et al., Current Protocols in Molecular Biology, Green Publishing Associates Wiley Interscience, New York.

What is needed then is an apparatus and method for replacing the use of large format gels for DNA sequencing, but does so without any loss of performance characteristics.

BRIEF SUMMARY OF THE INVENTION

The invention is an improvement in a method of DNA sequencing in a gel comprising the steps of providing a minigel cassette characterized by having reduced length and width. A DNA sequencing gel is then formed in the minigel cassette. A sample of DNA fragments is sequenced within the DNA sequencing gel in the minigel cassette without prewarming the DNA sequencing gel. The step of sequencing is performed at a reduced voltage. An image of sequenced DNA fragment bands is then produced within the DNA sequencing gel. The image is magnified within a computer to permit visual identification of the DNA bands. As a result, costs, expense and difficulties of handling large DNA sequencing gels are avoided.

In one embodiment the step of producing the image comprises the step of producing an autoradiograph. In other embodiments the step of producing the image is performed by chemiluminescent detection, florescent detection, radioactive detection, or staining followed by scanning.

In the illustrated method the step of producing the image further comprises the step of optically scanning the autoradiograph into the computer. The step of optical scanning is performed by scanning the autoradiograph with a CCD line camera.

The minigel cassette defines a DNA sequencing gel layer substantially smaller than 20×40 cm in width and length, respectively or more specifically, 8×11 cm in width and length, respectively or smaller.

The step of sequencing the DNA at a reduced voltage sequences the DNA within the gel defined within the minigel cassette at 500 volts or less.

The invention is also characterized as a system for sequencing DNA fragments comprising a minigel cassette for defining a DNA sequencing gel of substantially reduced size. An electrophoresis unit receives the minigel cassette to sequence the DNA fragments in the gel layer defined within the minigel cassette at a reduced voltage. A scanning mechanism scans the gel defined in the minicassette after the DNA sequence bands have been formed in the gel layer by actions of the electrophoresis unit. A computer is coupled to the scanning mechanism for receiving a detected pattern of the DNA bands in the gel layer and for magnifying the detected pattern for visual identification of nucleotide bases.

The invention may be better visualized by now turning to the following drawings wherein like elements are referenced by like numerals.

The invention and its various embodiments may now be understood by considering the following detailed description.

DETAILED DESCRIPTION OF THE PREFERRED EMBODIMENTS

The time, difficulty, and expense of running DNA sequencing gels is substantially reduced by running the DNA sequence in a minigel of approximately 8×11 cm at a reduced electrophoretic voltage and without preheating the buffer solution in contact with the gel. The image produced from the sequence gel or autoradiograph is then scanned with a CCD line camera. The pixel map of the autoradiograph image is then magnified using software techniques within the computer so that it is displayed on the CRT screen at an increased scale permitting easy visual separation between the DNA bands.

The sequencing method of the invention makes use of a small format gel electrophoresis system in a size of approximately 8 cm by 11 cm with virtually no loss of performance characteristics. The primary benefits of using small format gel systems are savings in time, labor, materials and space. For example, the time from beginning a sequencing experiment to having a DNA sequence entered into a computer can be reduced from a minimum of 16 to 24 hours to less than 6 hours by use of the present invention.

Small format gels are especially useful in reducing time and labor required in preparation of plates and pouring of gels. Another savings is in equipment, where power equipment in the electrophoresis system need only be capable of providing a relatively low voltage of 500 volts maximum. The gel holding apparatus can be the same as that used for protein minigels and further dramatic increases are predicted in the efficiency and the volume of DNA fragments that can be sequenced simultaneously in gel readers especially designed to handle the small format gel.

Figure 1:
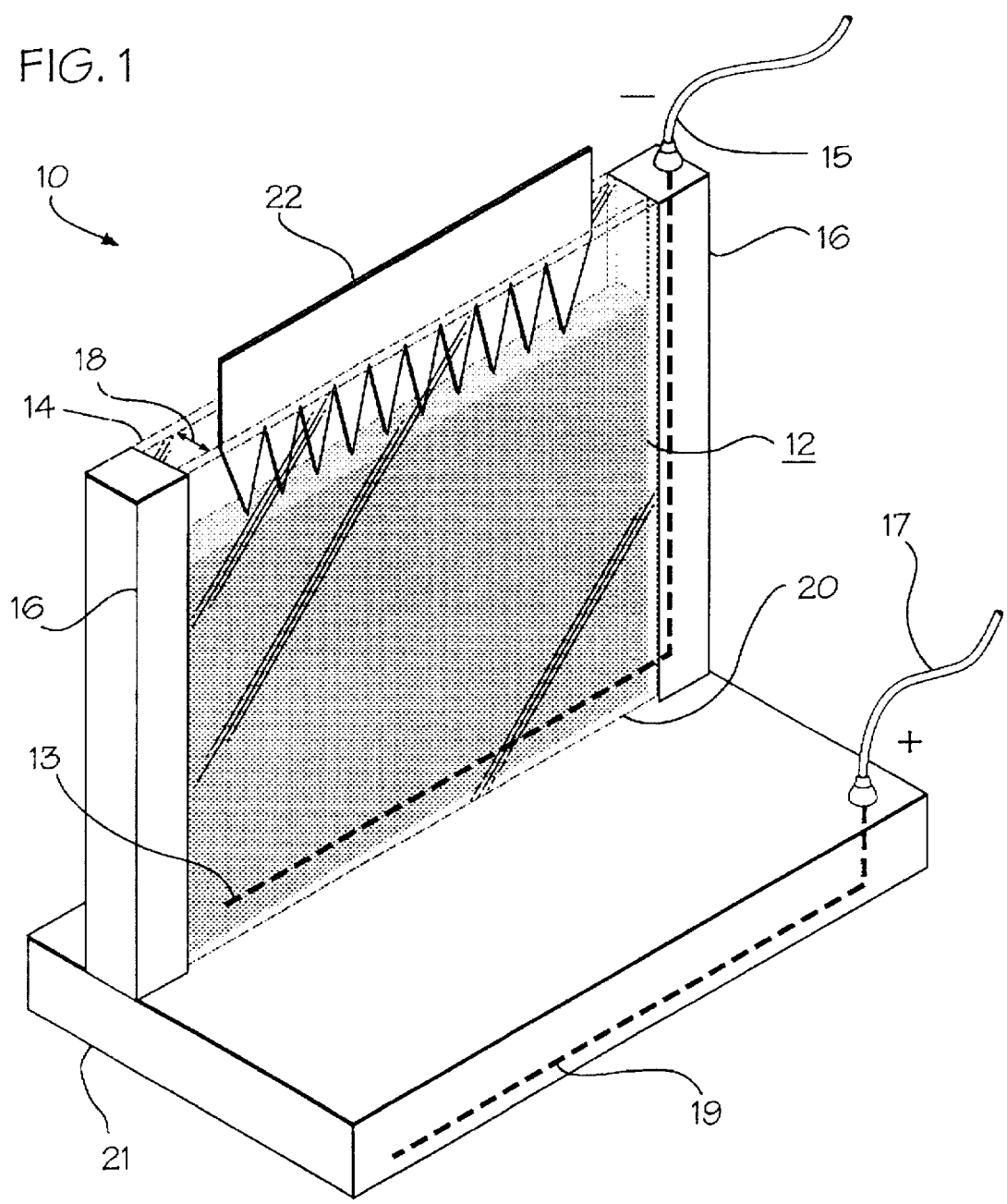
FIG. 1 is a simplified perspective view of a minigel cassette devised according to the invention.

In the illustrated embodiment, a commercially available 8×12 centimeter gel unit, sold under the trademark, TALL MIGHTY SMALL™ by Hoeffer Scientific Instruments of San Francisco, Calif., was used. The small format gels currently are designed for other electrophoresis applications other than DNA sequencing. This small unit accommodates an 8×11 centimeter gel cassette. As shown in FIG. 1, gel cassette, indicated generally by reference numeral 10, is comprised of an outer glass plate 12 disposed over an inner notched alumina plate 14. Alumina plate 14 remains in direct contact with an upper buffer chamber (not shown) over most of its length during the electrophoresis process. Lower buffer chamber 21 is shown in FIG. 1. A negative electrode terminal 15 is connected to a first wire electrode 13. A positive electrode terminal 17 is connected to a second wire electrode 19 between which electrode wires 13 and 19 the electrophoretic voltage is impressed. Alumina plate 14 is coated with a spreading agent sold under the mark, GEL SLICK™ by AT Biochemicals of Malvern, Pa. Glass plate 12 is spaced apart from alumina plate 14 by means of two parallel plastic spacers 16 thereby providing a gap 18 of approximately 0.4 millimeters between plates 12 and 14. A similar plastic strip (not shown) is placed across the lower edge 20 of gel cassette 10 while a conventional standard DNA sequencing gel is poured through gap 18 filling the space between plates 12 and 14. After the gel sets, the lower plastic spacer is removed.

The gel pouring process takes about 10 minutes from the time of assembling gel cassette 10 to pouring of the DNA sequencing gel. The smaller size of gel cassette 10 makes pouring these gels simpler and far easier than in the case of large format sequencing gels. For example, the inadvertent creation of an air bubble in the gel can destroy the gel as a usable unit. Since only approximately 5–10 milliliters of gel is used in the cassette of the invention as opposed to 75 to 120 milliliters in a standard DNA sequencing gel, the probability of creating such defects is substantially decreased.

The gels polymerize in about 20 minutes, although some degree of polymerization may continue for the next 24-hour period. Gel cassettes 10 may be stored in humid boxes for more than a week without any adverse effect on the sequencing ability of the gel. In the experiment described below, a double stranded plasmid DNA was isolated and cleaned with MAGIC MINIPREP™ kits sold by Promega Inc. of Madison, Wis. A normal workup procedure was performed for the DNA material sequencing reactions was done with minor modifications using SEQUENASE™ kits as sold by United States Biochemical Corporation of Ohio and [33P] dATP 2979Ci/mmol, manufactured by Dupont/NEN Inc. of Boston, Mass. The final volume of loading buffer for each reaction was 10 microliters. From this 0.5 to 1.0 microliters was loaded per lane in gel cassette 10. A shark's tooth comb 22 was disposed in gap 18 of gel cassette 10. In the illustrated embodiment, shark's tooth comb 22 was provided with 24 teeth. Because only ¹⁄₁₀ of the final volume is used for electrophoresis, the sequence reactions have been downsized.

The electrophoresis unit requires about 180 milliliters of prewarmed running buffer, 1×TBE (0.089M Tris-0.089M borate-0.0025M EDTA, pH 8.3). It was found, according to the invention, that electrophoresis buffer at room temperature works equally well. In fact, a prewarmed buffer may cause difficulties in loading the gel. It is important to note in this respect that the use of a very hot running buffer causes differential expansion within gel cassette 10 making loading difficult.

The gels within gel cassette 10 were then electrophoresed at 450 to 500 volts. In these conditions, it takes about 20 minutes for the bromophenyl blue front and about 55 minutes for the xylene-cyanol front to reach the bottom of the gel.

The gel, while still attached to glass plate 12, was fixed with 10 percent trichloroacetic acid for 1 to 2 minutes and transferred to WHATMAN™ filter paper, sold as 3 MM CHR™ by Whatman Laboratory Division in England. Thereafter, the gel was dried. The dried gel was autoradiographed using XAR 5™ film from Eastman Kodak Company in Rochester, N.Y. and/or RX™ film of Fuji Photo Film Company Ltd. of Japan with an intensifier for shorter exposure times and without an intensifier for longer exposure times. It was determined, according to the invention, that as a practical matter, 2 hour exposure is sufficient for reading the sequence. Longer exposures can be useful for confirmation.

Figure 2:
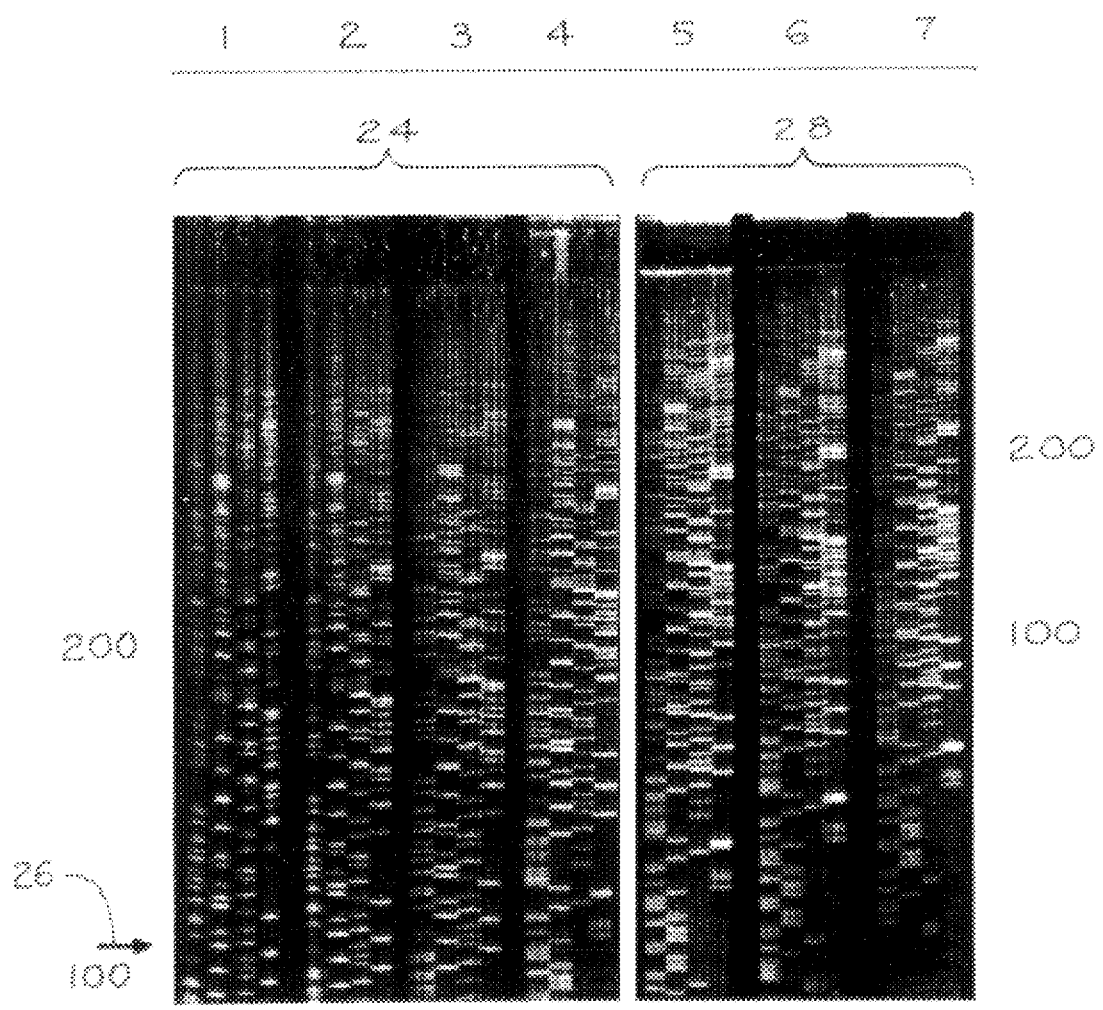
FIG. 2 is a life-size copy of an autoradiogram taken from the minigel of FIG. 1.

FIG. 2 shows an autoradiogram in life-size scale generated by electrophoresis of the sequencing reactions on a 6 percent polyacrylamide-TB-Eurea 8×11 centimeter minigel.

The results obtained with either alkali or heat-denatured DNA are comparable. The reaction sets in FIG. 2 were loaded within 3 to 5 minutes of each other. The reaction sets 1–4, indicated generally by reference numeral 24, represent one gel. DNA was denatured by alkali before sequencing and the gel in region 24 was run for about 55 minutes. The position of xylene-cyanol in the first load is shown by arrow 26 at the bottom of FIG. 2. The right three reactions sets 5–7, denoted generally by reference numeral 28, used heat-denatured DNA. The gel in these sets was run for about 20 to 25 minutes until the bromophenyl blue front reached the bottom of the gel. The numbers on the vertical scale of FIG. 2 indicate approximate distances (bp) from the primers in reaction sets 1 and 7, respectively.

Figure 3:
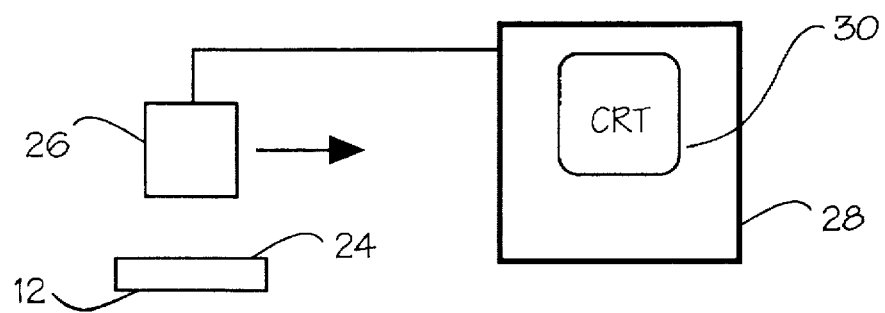
FIG. 3 is a simplified functional block diagram of a scanning and computer for reading the gels produced with the minigel cassette of FIG. 1.

The band in the lower part of the autoradiograph of FIG. 2 are easy to read, although the bands in the upper regions of the autoradiograph become visually demanding. This visual limitation is easily overcome by magnifying the autoradiograph. In the preferred embodiment, autoradiograph magnification is achieved by using a sequence film reader such as a BIOIMAGE™ sequence reader manufactured by Milli-Gen/Biosearch of Burlington, Mass. The sequence reader optically reads in the autoradiograph without optical magnification and loads the image into a pixel map into a computer. This is diagrammatically depicted in FIG. 3 where a gel layer 24 on glass plate 12 is scanned by a moving CCD camera 26. Scanning camera 26 has its output coupled to a conventional computer 28 which then displays a magnified view of selected portions of the autoradiograph of FIG. 2 upon a CRT screen 30. The additional use of optical magnification may be employed if desired, but under the present circumstances further magnification beyond that provided by the electronics of the system is unnecessary.

Figure 4:
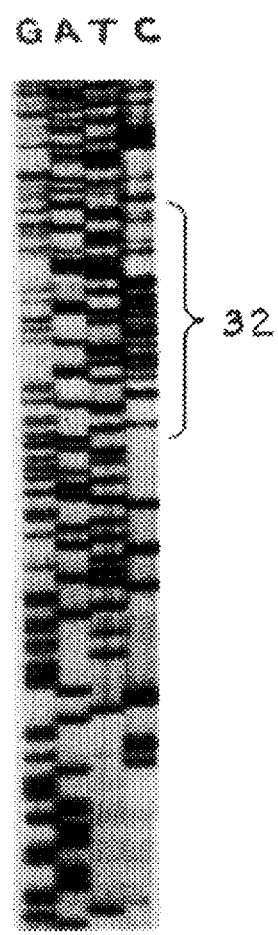
FIG. 4 is a photograph of four tracks of an autoradiograph magnified at a first magnification showing the sequencing of DNA fragments as taken from the depiction of FIG. 2.
Figure 5:
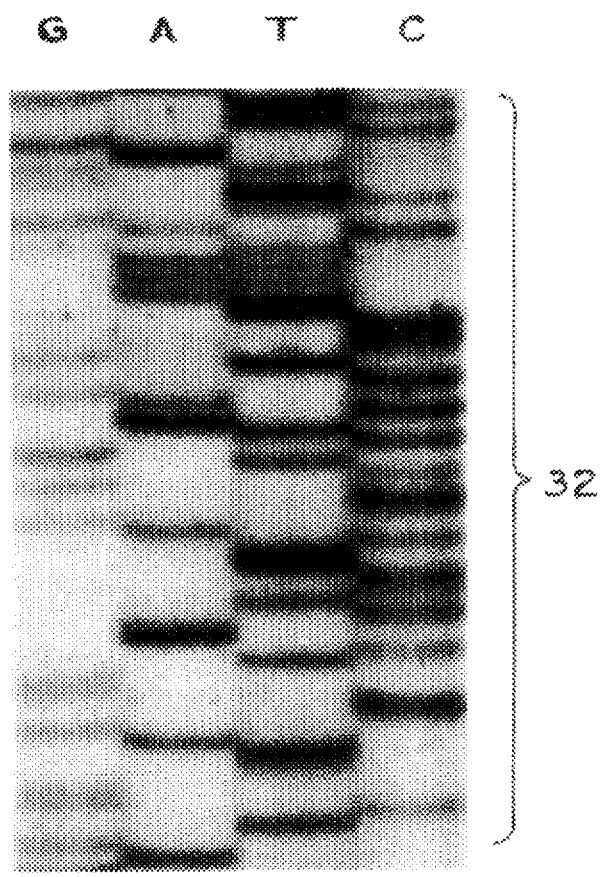
FIG. 5 is an enlargement of a portion of the tracks shown in FIG. 4.

FIG. 4 shows a magnified image of one set magnified in this manner from the autoradiograph of FIG. 2. The sequence rungs are clearly presented and if desired selected areas such as that generally indicated by reference numeral 32 can be further expanded by graphic expansion within computer 28 by conventional means to provide an expanded image of region 32 as shown in FIG. 5.

Figure 6A:
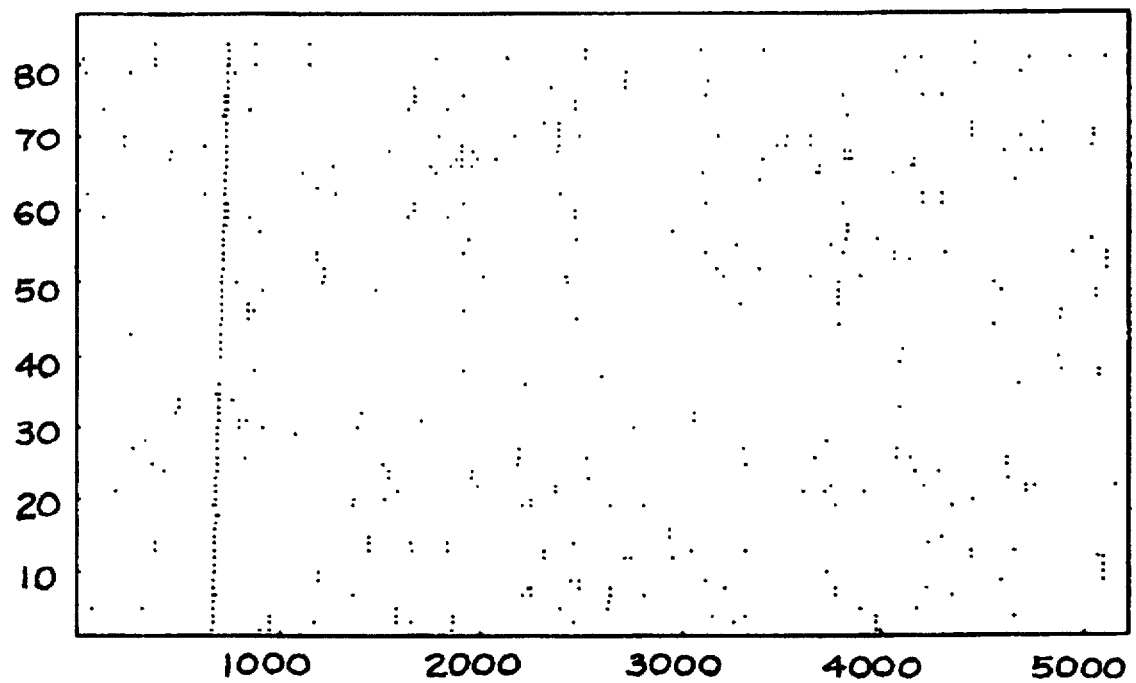
FIG. 6a is a dot matrix diagram of homologues of the sequences generated by the minigel of FIG. 1 done with a sequence of about 100 base pairs from a 6% gel.
Figure 6B:
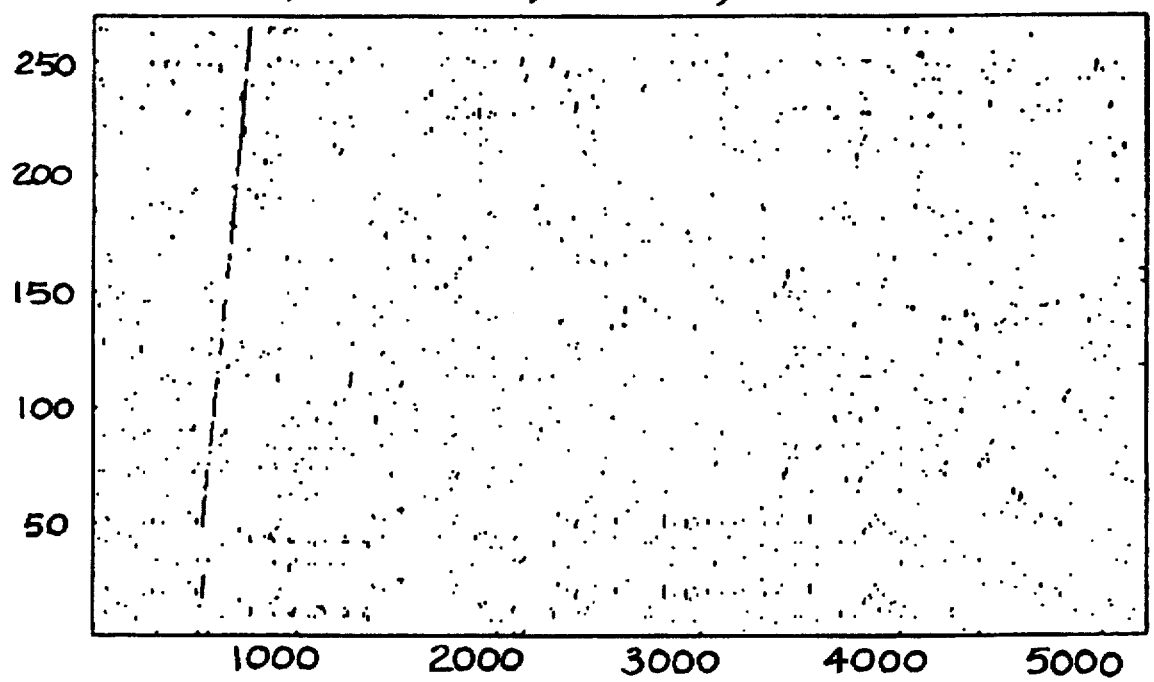
FIG. 6b is a dot matrix diagram of homologues of the sequences generated by the minigel of FIG. 1 done with a sequence of about 300 base pairs from a 4% and a 6% gel.

The reliability of the minigel of the invention is demonstrated in FIGS. 6a and 6b. Two kinds of cloned plasmid DNA's are sequenced. One of the plasmid DNA's was part of a larger (5 kb fragment) of a known sequence, while the other was an unknown cDNA clone. When used in a dot matrix analysis, the sequences generated from the known DNA molecules correctly matched their homologous positions in the known 5 kb sequence as shown by FIG. 6. The derived sequence on the X axis is part of the known sequence (the 5 kb fragment shown on the X axis). In FIG. 6a, analysis done with a sequence of about 100 bp was derived with a 6% gel. Analysis was also done with a sequence of about 300 bp derived from a 4% and 6% gel. The sequences used for dot matrix analysis were read only once without revisions and corrections using GENEPRO™ as manufactured by Riverside Scientific Enterprises of Washington.

The dot matrix search for homologous sequences generated by the minigel sequencing as shown in FIGS. 6a and 6b clearly establishes the reliability of the sequences attained from the minigel autoradiograms and their utility in determining the sequence content of a fragment or clone in question. In this example, the unknown DNA was sequenced both on a large 20×40 centimeter format gel, and on an 8×11 centimeter minigel. Comparison of the two sequences showed only that the differences encountered were in homopolymer runs. The exact number of bases in homopolymer run could not be correctly read in the minigel autoradiograph. Since homopolymer stretches are only a minimal part of an average DNA sequence, this limitation does not detract in any way from the usefulness of the minigel.

It is expected that minigel sequencing can be used for a quick assessment of the sequence content of a DNA fragment as is used in various protocols, such as screening, protein engineering, site-directed mutagenesis, and DNA polymorphism studies. With the disclosed methodology, sequences from the two ends of a clone fragment can be determined within six hours, starting from an overnight culture.

The disclosed technique provides considerable ease of operation and remarkable savings in time, materials and bench space. The equipment is simple, inexpensive and can readily be adapted from commercially available equipment, or fabricated locally. No special power supplies are required for electrophoresis.

It is contemplated that multiple 8×11 centimeter gels may be run simultaneously, or independently, each with independent parameters of time and gel strengths. For example, a 4 and 8% gel could be run at the same time to read at two different distances from the primer. Further, considering the ease of handling, minigel sequencing can become the method of choice for chemiluminescent detection of sequence ladders. Improvements in automated sequencing technology can be realized through the analysis of smaller sequence ladders as developed in an in-gel detection of radioactive or fluorescent bands.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the essential idea of the invention.

I claim:

1. An improvement in a method of DNA sequencing in a gel comprising the steps of:

providing a minigel cassette characterized by having reduced length and width with the largest dimension thereof being less than approximately 20 cm;

preparing a DNA sequencing gel in said minigel cassette;

sequencing a sample of DNA fragments within said DNA sequencing gel in said minigel cassette without pre-warming said DNA sequencing gel from room temperature, said step of sequencing being performed at a reduced voltage compared to voltage levels used in large cassettes with the smallest width or length dimension thereof being more than approximately 20 cm to obtain a sequence ladder resolution of a single base pair; and producing an image of sequenced DNA fragment bands within said DNA sequencing gel;

scanning said image with a CCD camera to produce a computer-magnifiable digital image to permit visual identification of said single base pair among said DNA bands without any loss of performance characteristics.

2. The method of claim 1 wherein said step of producing said image comprises the step of producing an autoradiograph.

3. The method of claim 1 wherein said step of producing said image comprises the step of staining said gel.

4. The method of claim 1 where said step of producing said image is performed by chemiluminescent detection and scanning.

5. The method of claim 1 where said step of producing said image is performed by florescent detection and scanning.

6. The method of claim 1 wherein said step of producing said image is formed by radioactive detection and scanning.

7. The method of claim 1 where said step of producing said image comprises the step of optically scanning said image into said computer.

8. The method of claim 7 where said step of optical scanning is performed by scanning said autoradiograph with a CCD line camera.

9. The method of claim 1 wherein said minigel cassette defines a DNA sequencing gel layer smaller than 20×40 cm in width and length, respectively such that at such smaller size resolution of DNA bands is normally expected to be unreliable.

10. The method of claim 1 where said step of providing said minigel cassette defines a DNA sequencing gel therein 8×11 cm in width and length, respectively, or smaller.

11. The method of claim 1 where said step of sequencing said DNA at a reduced voltage sequences said DNA within said gel defined within said minigel cassette at 500 volts or less.

12. A system for sequencing DNA fragments comprising:

a minigel cassette for defining a DNA sequencing gel of substantially reduced size with the largest dimension thereof being less than approximately 20 cm;

a electrophoresis unit for receiving said minigel cassette to sequence said DNA fragments in said gel layer defined within said minigel cassette at a reduced voltage substantially at room temperature without external addition of heat to said minigel cassette;

a scanning mechanism for scanning said gel defined in said minigel cassette after said DNA sequence bands have been formed in said gel layer by actions of said electrophoresis unit; and a computer coupled to said scanning mechanism for receiving a detected pattern of said DNA bands in said gel layer and for digitally magnifying said detected pattern for visual identification of a single nucleotide base without any loss of performance characteristics.

13. The system of claim 12 further comprising means for producing an autoradiogram of said DNA bands within said gel defined in said minigel cassette and wherein said scanning mechanism is an optical scanning CCD line camera.

14. The system of claim 12 wherein said scanning mechanism is a chemiluminescent detector and scanner.

15. The system of claim 12 wherein said scanning mechanism is a florescent detector and scanner.

16. The system of claim 12 wherein said scanning mechanism is a radioactive detector and scanner.

17. The system of claim 12 wherein said gel layer defined in said minigel cassette is smaller than 20×40 cm in width and length, respectively, such that at such smaller size resolution of DNA bands is normally expected to be unreliable.

18. The system of claim 17 wherein said gel layer defined in said minigel cassette is 8×11 cm in length and width, respectively, or smaller.

19. The system of claim 12 wherein said electrophoresis unit operates at electrophoretic voltage of 500 volts or less.

20. A method of sequencing DNA fragments comprising the steps of:

electrophoretically producing said DNA sequence in a DNA sequencing gel of reduced length with the largest dimension thereof being less than approximately 20 cm at a reduced voltage as compared to larger sized gels with the smallest width or length dimension thereof being more than approximately 20 cm with a room temperature buffer in thermal contact with said DNA sequencing gel;

producing an image of DNA sequence bands from said DNA sequencing gel;

digitally magnifying said image in a computer to provide visual separation between said DNA fragment bands in said image; and identifying a single nucleotide base from said magnified image without any loss of performance characteristics.

21. The method of claim 20 where said step of magnifying said image is performed within a computer by displaying a pixel map of said image in magnified scale on an output screen of said computer.

* * * * *